(12) United States Patent
Weadock et al.

(10) Patent No.: US 8,556,797 B2
(45) Date of Patent: Oct. 15, 2013

(54) MAGNETIC IMPLANTS FOR TREATING OBSTRUCTIVE SLEEP APNEA AND METHODS THEREFOR

(75) Inventors: Kevin Weadock, Hillsborough, NJ (US); Robert A. Rousseau, Ottsville, PA (US)

(73) Assignee: Ethicon, Inc., Somerville, NJ (US)

( * ) Notice: Subject to any disclaimer, the term of this patent is extended or adjusted under 35 U.S.C. 154(b) by 932 days.

(21) Appl. No.: 12/183,955

(22) Filed: Jul. 31, 2008

(65) Prior Publication Data

US 2010/0030011 A1 Feb. 4, 2010

(51) Int. Cl.
*A61F 2/00* (2006.01)

(52) U.S. Cl.
USPC .......................................................... 600/37

(58) Field of Classification Search
USPC ................ 600/12, 37; 602/60, 263, 264, 902; 128/860, 848, 897–899
See application file for complete search history.

(56) References Cited

U.S. PATENT DOCUMENTS

| | | |
|---|---|---|
| 3,123,077 A | 3/1964 | Alcamo |
| 3,378,010 A | 4/1968 | Codling et al. |
| 4,069,825 A | 1/1978 | Akiyama |
| 4,290,763 A | 9/1981 | Hurst |
| 4,557,264 A | 12/1985 | Hinsch |
| 4,839,215 A | 6/1989 | Starling et al. |
| 4,881,939 A | 11/1989 | Newman |
| 4,950,285 A | 8/1990 | Wilk |
| 5,053,047 A | 10/1991 | Yoon |
| 5,123,913 A | 6/1992 | Wilk et al. |
| 5,269,783 A | 12/1993 | Sander |
| 5,284,161 A | 2/1994 | Karell |
| 5,311,028 A | 5/1994 | Glavish |
| 5,393,984 A | 2/1995 | Glavish |
| 5,483,077 A | 1/1996 | Glavish |
| 5,484,444 A | 1/1996 | Braunschweiler et al. |
| 5,609,559 A | 3/1997 | Weitzner |
| 5,683,417 A | 11/1997 | Cooper |
| 5,704,895 A | 1/1998 | Scott et al. |

(Continued)

FOREIGN PATENT DOCUMENTS

| | | |
|---|---|---|
| CN | 2465680 Y | 12/2001 |
| CN | 102198010 A | 9/2011 |

(Continued)

OTHER PUBLICATIONS

The Pillar Procedure, Restore Medical, Inc., www.restoremedical.com, 2 pp., Sep. 6, 2008.

(Continued)

*Primary Examiner* — Samuel Gilbert

(57) ABSTRACT

A magnetic implant for treating sleep disorders includes a first anchor, a first magnet coupled to the first anchor, a tongue anchor, a second magnet coupled to the tongue anchor, and a support for aligning the first and second magnets so that a repelling force is generated between the magnets for urging the second magnet away from the first magnet. In one embodiment, the support aligns a magnetic pole of the first magnet with a repelling magnetic pole of the second magnet, guides movement of the first and second magnets relative to one another, and maintains the first magnet at a fixed distance from the first anchor. In one embodiment, the repelling force urges the second magnet toward the first anchor. The first anchor may be connected to bone or soft tissue.

27 Claims, 8 Drawing Sheets

(56) References Cited

U.S. PATENT DOCUMENTS

| | | |
|---|---|---|
| 5,792,067 A | 8/1998 | Karell |
| 5,843,077 A | 12/1998 | Edwards |
| 5,931,855 A | 8/1999 | Burke |
| 6,161,541 A | 12/2000 | Woodson |
| 6,241,747 B1 | 6/2001 | Ruff |
| 6,250,307 B1 | 6/2001 | Conrad et al. |
| 6,348,156 B1 | 2/2002 | Vishnoi et al. |
| 6,431,174 B1 | 8/2002 | Knudson et al. |
| 6,432,437 B1 | 8/2002 | Hubbard |
| 6,457,472 B1 | 10/2002 | Schwartz et al. |
| 6,513,530 B2 | 2/2003 | Knudson et al. |
| 6,523,542 B2 | 2/2003 | Knudson et al. |
| 6,578,580 B2 | 6/2003 | Conrad et al. |
| 6,589,549 B2 | 7/2003 | Shih et al. |
| 6,599,310 B2 | 7/2003 | Leung et al. |
| 6,627,600 B2 | 9/2003 | Boutignon |
| 6,634,362 B2 | 10/2003 | Conrad et al. |
| 6,638,284 B1 | 10/2003 | Rousseau et al. |
| 6,716,251 B1 | 4/2004 | Asius et al. |
| 6,742,524 B2 | 6/2004 | Knudson et al. |
| 6,755,868 B2 | 6/2004 | Rousseau |
| 6,800,082 B2 | 10/2004 | Rousseau |
| 6,899,105 B2 | 5/2005 | Krueger et al. |
| 6,955,172 B2 | 10/2005 | Nelson et al. |
| 6,981,944 B2 | 1/2006 | Jamiolkowski et al. |
| 7,017,582 B2 | 3/2006 | Metzger et al. |
| 7,056,331 B2 | 6/2006 | Kaplan et al. |
| 7,135,189 B2 | 11/2006 | Knapp |
| 7,146,981 B2 | 12/2006 | Knudson et al. |
| 7,166,570 B2 | 1/2007 | Hunter et al. |
| 7,213,599 B2 | 5/2007 | Conrad et al. |
| 7,237,554 B2 | 7/2007 | Conrad et al. |
| 7,288,075 B2 | 10/2007 | Parihar et al. |
| 7,297,102 B2 | 11/2007 | Smith et al. |
| 7,322,993 B2 | 1/2008 | Metzger et al. |
| 7,337,781 B2 | 3/2008 | Vassallo |
| 7,360,432 B2 | 4/2008 | Lehtonen |
| 7,360,542 B2 | 4/2008 | Nelson et al. |
| 7,367,340 B2 | 5/2008 | Nelson et al. |
| 7,401,611 B2 | 7/2008 | Conrad et al. |
| 7,442,389 B2 | 10/2008 | Quelle et al. |
| 7,601,164 B2 | 10/2009 | Wu |
| 7,669,603 B2 | 3/2010 | Knudson et al. |
| 7,806,908 B2 | 10/2010 | Ruff |
| 7,850,894 B2 | 12/2010 | Lindh, Sr. et al. |
| 7,857,829 B2 | 12/2010 | Kaplan et al. |
| 7,888,119 B2 | 2/2011 | Sugaya et al. |
| 8,142,422 B2 | 3/2012 | Makower et al. |
| 2001/0037133 A1 | 11/2001 | Knudson et al. |
| 2003/0004579 A1 | 1/2003 | Rousseau et al. |
| 2003/0034312 A1 | 2/2003 | Unger et al. |
| 2003/0149445 A1 | 8/2003 | Knudson et al. |
| 2003/0149447 A1 | 8/2003 | Morency et al. |
| 2003/0176875 A1 | 9/2003 | Anderson et al. |
| 2004/0020492 A1 | 2/2004 | Dubrul et al. |
| 2004/0020498 A1 | 2/2004 | Knudson et al. |
| 2004/0028676 A1 | 2/2004 | Klein et al. |
| 2004/0102796 A1 | 5/2004 | Hill et al. |
| 2004/0139975 A1 | 7/2004 | Nelson et al. |
| 2004/0144395 A1 | 7/2004 | Evans et al. |
| 2004/0147811 A1 | 7/2004 | Diederich et al. |
| 2004/0149290 A1 | 8/2004 | Nelson et al. |
| 2004/0153127 A1 | 8/2004 | Gordon et al. |
| 2004/0231678 A1 | 11/2004 | Fierro |
| 2005/0038472 A1 | 2/2005 | Furst |
| 2005/0082452 A1 | 4/2005 | Kirby |
| 2005/0092334 A1 | 5/2005 | Conrad et al. |
| 2005/0115572 A1 | 6/2005 | Brooks et al. |
| 2005/0121039 A1 | 6/2005 | Brooks et al. |
| 2005/0159637 A9 | 7/2005 | Nelson et al. |
| 2005/0165352 A1 | 7/2005 | Henry et al. |
| 2005/0199248 A1 | 9/2005 | Pflueger et al. |
| 2005/0203576 A1 | 9/2005 | Sulamanidze |
| 2005/0251255 A1 | 11/2005 | Metzger et al. |
| 2005/0267321 A1 | 12/2005 | Shadduck |
| 2005/0267531 A1 | 12/2005 | Ruff et al. |
| 2005/0267532 A1 | 12/2005 | Wu |
| 2005/0267571 A1* | 12/2005 | Spence et al. ............... 623/2.11 |
| 2005/0279365 A1 | 12/2005 | Armijo et al. |
| 2006/0005843 A9 | 1/2006 | Nelson et al. |
| 2006/0079935 A1 | 4/2006 | Kolster |
| 2006/0083767 A1 | 4/2006 | Deusch et al. |
| 2006/0093644 A1 | 5/2006 | Quelle et al. |
| 2006/0150986 A1 | 7/2006 | Roue et al. |
| 2006/0185673 A1 | 8/2006 | Critzer et al. |
| 2006/0206197 A1 | 9/2006 | Morsi |
| 2006/0207608 A1 | 9/2006 | Hirotsuka et al. |
| 2006/0207612 A1 | 9/2006 | Jackson et al. |
| 2006/0228391 A1 | 10/2006 | Seyedin et al. |
| 2006/0241339 A1 | 10/2006 | Cook et al. |
| 2006/0266369 A1* | 11/2006 | Atkinson et al. ............... 128/848 |
| 2006/0289015 A1 | 12/2006 | Boucher et al. |
| 2007/0000497 A1 | 1/2007 | Boucher et al. |
| 2007/0005109 A1 | 1/2007 | Popadiuk et al. |
| 2007/0005110 A1 | 1/2007 | Collier et al. |
| 2007/0102010 A1 | 5/2007 | Lemperle et al. |
| 2007/0110788 A1 | 5/2007 | Hissong et al. |
| 2007/0119463 A1 | 5/2007 | Nelson et al. |
| 2007/0123996 A1 | 5/2007 | Sugaya et al. |
| 2007/0144531 A1 | 6/2007 | Tomas et al. |
| 2007/0144534 A1 | 6/2007 | Mery et al. |
| 2007/0144535 A1 | 6/2007 | Hegde et al. |
| 2007/0190108 A1 | 8/2007 | Datta et al. |
| 2007/0204866 A1 | 9/2007 | Conrad et al. |
| 2007/0209665 A1 | 9/2007 | Gillis et al. |
| 2007/0227545 A1 | 10/2007 | Conrad et al. |
| 2007/0233276 A1 | 10/2007 | Conrad et al. |
| 2007/0246052 A1 | 10/2007 | Hegde et al. |
| 2007/0256693 A1 | 11/2007 | Paraschac et al. |
| 2007/0257395 A1 | 11/2007 | Lindh et al. |
| 2007/0261701 A1 | 11/2007 | Sanders |
| 2007/0270631 A1 | 11/2007 | Nelson et al. |
| 2007/0272257 A1 | 11/2007 | Nelson et al. |
| 2007/0288057 A1 | 12/2007 | Kuhnel |
| 2007/0295338 A1 | 12/2007 | Loomas et al. |
| 2007/0295340 A1 | 12/2007 | Buscemi |
| 2008/0023012 A1 | 1/2008 | Dineen et al. |
| 2008/0035158 A1 | 2/2008 | Pflueger et al. |
| 2008/0035160 A1 | 2/2008 | Woodson et al. |
| 2008/0066764 A1 | 3/2008 | Paraschac et al. |
| 2008/0066765 A1 | 3/2008 | Paraschac et al. |
| 2008/0066767 A1 | 3/2008 | Paraschac et al. |
| 2008/0066769 A1 | 3/2008 | Dineen et al. |
| 2008/0078411 A1 | 4/2008 | Buscemi et al. |
| 2008/0146868 A1 | 6/2008 | Robert et al. |
| 2008/0167614 A1 | 7/2008 | Tolkowsky et al. |
| 2008/0199824 A1 | 8/2008 | Hargadon |
| 2008/0208265 A1 | 8/2008 | Frazier et al. |
| 2008/0221684 A1 | 9/2008 | Nelson et al. |
| 2008/0312688 A1 | 12/2008 | Nawrocki et al. |
| 2009/0025734 A1 | 1/2009 | Doelling et al. |
| 2009/0078411 A1 | 3/2009 | Kenison et al. |
| 2009/0165803 A1 | 7/2009 | Bhat et al. |
| 2010/0023055 A1 | 1/2010 | Rousseau |
| 2010/0024830 A1 | 2/2010 | Rousseau |
| 2010/0030011 A1 | 2/2010 | Weadock et al. |
| 2010/0037901 A1 | 2/2010 | Rousseau |
| 2010/0080791 A1 | 4/2010 | Rousseau |
| 2010/0106246 A1 | 4/2010 | Rousseau |
| 2010/0108077 A1 | 5/2010 | Lindh |
| 2010/0132719 A1 | 6/2010 | Jacobs |
| 2010/0137794 A1 | 6/2010 | Knudson et al. |
| 2010/0137905 A1 | 6/2010 | Weadock et al. |
| 2010/0163056 A1 | 7/2010 | Tschopp et al. |
| 2010/0211184 A1 | 8/2010 | Rousseau |
| 2010/0234794 A1 | 9/2010 | Weadock |
| 2010/0234946 A1 | 9/2010 | Rousseau |
| 2010/0294284 A1 | 11/2010 | Hohenhorst et al. |
| 2010/0319710 A1 | 12/2010 | Sharkawy et al. |
| 2011/0100376 A1 | 5/2011 | Rousseau |
| 2011/0100377 A1 | 5/2011 | Weadock et al. |
| 2011/0100378 A1 | 5/2011 | Rousseau |
| 2011/0144558 A1 | 6/2011 | Rousseau |
| 2011/0174315 A1 | 7/2011 | Zhang et al. |

(56) References Cited

U.S. PATENT DOCUMENTS

| | | | |
|---|---|---|---|
| 2011/0178439 A1 | 7/2011 | Irwin et al. |
| 2012/0245629 A1 | 9/2012 | Gross et al. |
| 2013/0074849 A1 | 3/2013 | Rousseau et al. |
| 2013/0098371 A1 | 4/2013 | Rousseau et al. |
| 2013/0118505 A1 | 5/2013 | Rousseau et al. |
| 2013/0150872 A1 | 6/2013 | Rousseau |
| 2013/0174857 A1 | 7/2013 | Rousseau et al. |
| 2013/0186412 A1 | 7/2013 | Weadock et al. |

FOREIGN PATENT DOCUMENTS

| | | |
|---|---|---|
| DE | 10245076 A1 | 4/2004 |
| DE | 10245076 B4 | 4/2004 |
| EP | 2145587 A2 | 1/2010 |
| EP | 2517633 A1 | 10/2012 |
| FR | 2651113 A1 | 3/1991 |
| JP | 2003265621 | 9/2003 |
| SU | 927236 B | 5/1982 |
| WO | 9900058 | 1/1999 |
| WO | 0066050 | 11/2000 |
| WO | 0121107 | 3/2001 |
| WO | 03/096928 A1 | 11/2003 |
| WO | 2004/021869 A2 | 3/2004 |
| WO | 2004021870 | 3/2004 |
| WO | 2004060311 | 7/2004 |
| WO | 2004084709 | 10/2004 |
| WO | 2005046554 | 5/2005 |
| WO | 2005051292 | 6/2005 |
| WO | 2005082452 | 9/2005 |
| WO | 2005122954 | 12/2005 |
| WO | 2006012188 | 2/2006 |
| WO | 2004020492 | 4/2006 |
| WO | 2006072571 | 7/2006 |
| WO | 2006108145 | 10/2006 |
| WO | 2007056583 | 5/2007 |
| WO | 2007075394 | 7/2007 |
| WO | 2007134005 | 11/2007 |
| WO | 20070132449 | 11/2007 |
| WO | 2007146338 | 12/2007 |
| WO | 2007149489 | 12/2007 |
| WO | 2008118913 | 10/2008 |
| WO | 2009023256 | 2/2009 |
| WO | 2009036094 | 3/2009 |
| WO | 2010/019376 A2 | 2/2010 |
| WO | 2010/035303 A1 | 4/2010 |
| WO | 2010653411 | 6/2010 |
| WO | 2012/041205 A1 | 4/2012 |
| WO | 2012/064902 A1 | 5/2012 |
| WO | 2012/170468 | 12/2012 |

OTHER PUBLICATIONS

Pang, Kenny et al., "Tongue Suspension Suture in Obstructive Sleep Apnea," Operative Techniques in Otolaryngology, vol. 17, No. 4, Dec. 2006, pp. 252-256.
The Advance System, Aspire Medical, Inc., www.aspiremedical,com, 3 pp., Sep. 6, 2008.
Cole et al., "Snoring: A Review and a Reassessment", J. of Otolaryngology, pp. 303-306 (1995).
Harries at al., "The Surgical treatment of snoring", J. of Laryrngology and Otology, pp. 1105-1106 (1996).
Huang et al. "Bomeohanios of snoring", Endeavour, vol. 19(3): pp. 96-100 (1995).
Schwab , "Upper airway and soft tissue changes induced by CPAP in norm subject", Am. J. Respit. Crit. Care Med., vol. 154, No. 4, Oct. 1996, pp. 1106-1116.
Schwartz at al., "Effects of electrical stimulation to the soft palate on snoring and obstructive steep apnea", J. Prosthetic Dentistry, pp. 273-281 (1986).

Teles et al,. "Use of Palatal Lift Prosthesis on Patient Submitted to Maxillectomy: A Case Report", Applied Can Res. 2005, vol. 25(3), pp. 151-154.
Vicente at al., "Tongue-Base Suspension in Conjunction with Uvulopapatopharyngoplasty for Treatement of Severe Obstructive Sleep Apnea: Long-term Follow-Up Results", The Laryngoscope, vol. 115(7), pp. 1223-1227 (2006).
Wassmuth at al. "Cautery-assisted palatel stiffening operation for the treatment of obstructive sleep apnea syndrome", Otolaryngology— Head and Neck. Surgery, vol. 123(1), pp. 55-60 (Jul. 2000).
Wiltfang at al., "First results on daytime submandibular electrostimulation of suprahyoldal muscles to prevent night-time hypopharyngeal collapse in obstructive sleep apnea syndrom", Intl J. Of Oral & Maxillofacial Surgery. pp. 21-25 (1999).
Notification of Transmittal of the International Search Report and the Written Opinion of the International Search Authority or the Declaration mailed on Feb. 3, 2010 for; PCT1US20091051921; International Filing Date: Jul. 28, 2009.
Notification of Transmittal of the International Search Report and the Written Opinion of the International Search Authority or the Declaration mailed on May 25, 2010, PCT/US2010/023152; International Filing Date: Apr. 2, 2010.
International Search Report dated Dec. 21 2009 for International Patent Application No. PCT/US2009/057661.
International Search Report dated Apr. 29, 2010 for International Patent Application No. PCT/US2009/065293.
International Search Report dated May 25, 2010 for International Patent Application No. PCT/US2010/025778.
International Search Report dated Dec. 22, 2009 for International Patent Application No. PCT/US2009/061223.
The Pillar Procedure, Restore Medical, Inc., www.restoremedical.com, 2 pages, Sep. 6, 2008.
Repose Genioglossus Advancement, INFLUENT Medical, www.influ.ent.com, 1 page, Sep. 6, 2008.
Pang, Kenny et al., "Tongue Suspension Suture in Obstructive Sleep Apnea," Operative Techniques in Otolaryngology, vol. 17, No. 4, Dec. 2006, pp. 252-256, Sep. 6, 2008.
The Advance System, Aspire Medical, Inc., www.aspiremedical,com, 3 pages, Sep. 6, 2008.
Scfileef et at., Cytokine Activation of Vascular Endothelium Effects on Tissue-Type 1 Plasminogen Activator Inhibitor; The J. of Biological Chem,: vol. 263(12), 1988, pp. 5797-5803.
Shamsuzzaman et at.. "Obstructive Sleep Apnea; Implications for Cardiac and Vascular Disease," JAMA vol. 290 (14); pp. 1906-1914: 2003.
Shamsuzzaman et al., "Obstructive Sleep Apnea; Implications for Cardiac and Vascular Disease", JAMA vol. 290, No. 14 pp. 1909-1914 (2003).
International Search Report dated Dec. 29, 2009 for International Patent Application No. PCT/US2009/061455.
International Search Report dated Jan. 21, 2010 for International Patent Application No. PCT/US2009/052110.
International Search Report dated Jan. 14, 2011 for International Patent Application No. PCT/US2010/052628.
International Search Report dated Jan. 20, 2011 for International Patent Application No. PCT/US2010/052644.
International Search Report dated Jan. 24, 2011 for International Patent Application No. PCT/US2010/052649.
International Search Report dated Feb. 28, 2011 for International Patent Application No. PCT/US2010/059673.
International Search Report dated Apr. 9, 2013 for International Patent Application No. PCT/US2012/061569.
International Search Report dated Apr. 2, 2013 for International Patent Application No. PCT/US2012/067708.
U.S. Appl. No. 13/486,293 filed Jun. 1, 2012.
International Search Report dated May 25, 2010 for International Patent Application No. PCT/US2010/023152.
Written Opinion dated Nov. 27, 2012 for International Patent Application No. PCT/US2012/056577.

* cited by examiner

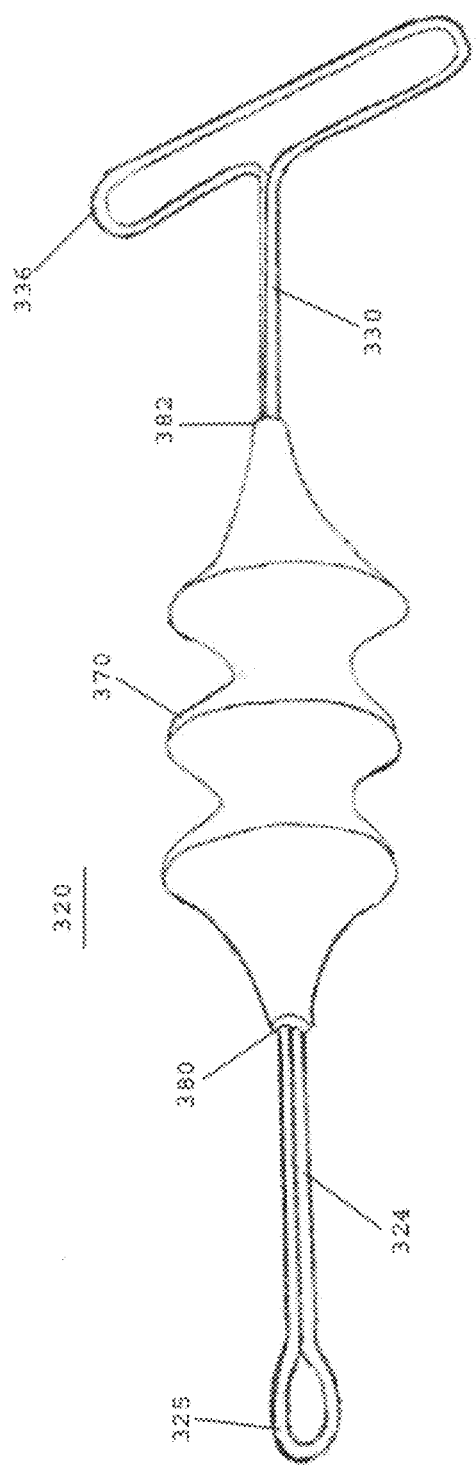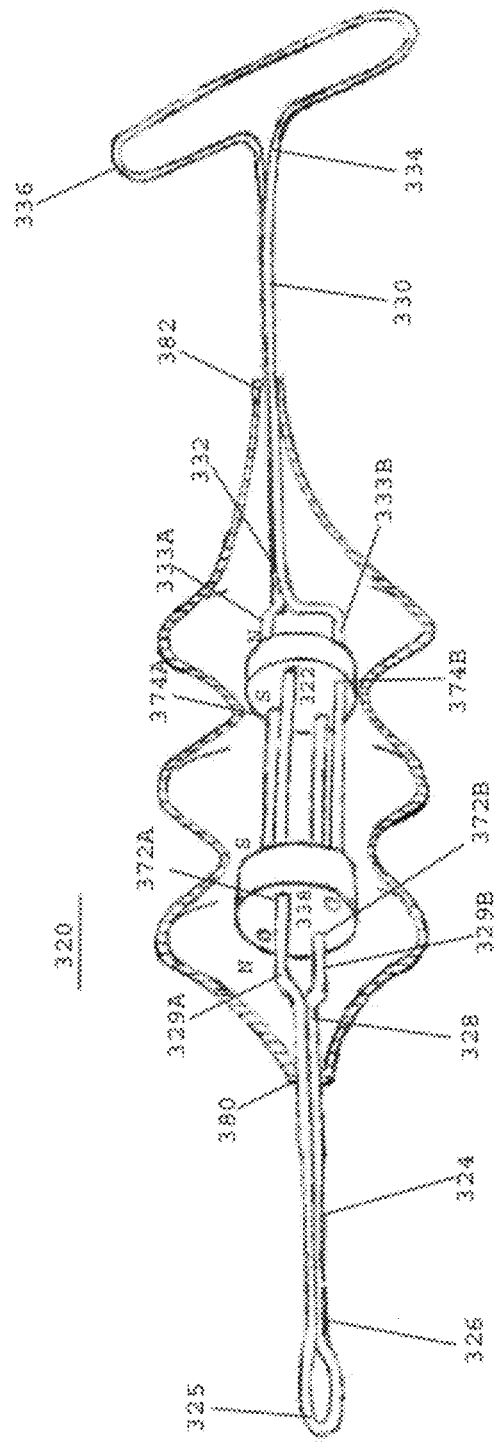

MAGNETIC IMPLANTS FOR TREATING OBSTRUCTIVE SLEEP APNEA AND METHODS THEREFOR

BACKGROUND OF THE INVENTION

1. Field of the Invention

The present invention generally relates to treating sleep disorders, and more specifically relates to systems, devices and methods for treating sleep disorders such as obstructive sleep apnea.

2. Description of the Related Art

Obstructive sleep apnea (OSA) is caused by a blockage of the upper airway that occurs when the soft tissue in the throat collapses during sleep. During each OSA event, the brain briefly arouses the sleeping individual in order resume breathing. This type of sleep is extremely fragmented and of poor quality. When left untreated, OSA may result in various problems including sleepiness, high blood pressure, cardiovascular disease, weight gain, impotency, headaches, memory problems, job impairment, and motor vehicle crashes.

According to the National Institutes of Health, OSA is very common and affects more than twelve million Americans. Risk factors include being a male and being overweight. Another risk factor includes being over 40 years old; however, OSA can strike at any age. Despite the significant medical consequences of OSA, a lack of awareness by the public and healthcare professionals results in the vast majority of OSA sufferers remaining undiagnosed and untreated.

There have been a number of efforts directed to treating OSA. Perhaps the most widely-used treatment is referred to as continuous positive airway pressure (CPAP), whereby air under positive pressure is delivered into the upper airway through a specially designed nasal mask or pillow. When the patient inhales, the flow of high-pressure air keeps the airway open. CPAP is considered to be one of the most effective non-surgical treatments for alleviating OSA. However, CPAP patients complain about discomfort from the mask and hoses, bloating, nasal drying, and dry eyes. Thus, patient compliance is relatively poor (i.e. about 40% compliance).

U.S. Pat. Nos. 5,284,161 and 5,792,067 disclose devices for treating OSA that electrically stimulate the soft palate. These electrical stimulation devices have also had mixed results because of poor patient compliance, patient discomfort during sleep, and repeated arousal of the patient throughout the night.

In order to minimize the need for patient compliance, surgical methods for treating OSA have also been developed. One surgical method, referred to as uvulopalatopharyngoplasty, involves removing about 2 cm of the trailing edge of the soft palate to reduce the soft palate's ability to block the upper airway. Another procedure uses a surgical laser to create scar tissue on the surface of the soft palate. The scar tissue reduces the flexibility of the soft palate, which, in turn, reduces snoring and/or closing of the upper airway passage.

There are a number of problems associated with the above-described surgical procedures. First, the area subjected to surgical treatment (e.g. removal of palatal tissue or scarring of palatal tissue) may be larger than is necessary to treat the patient's condition. In addition, the surgical procedures are painful, and have extended and uncomfortable healing periods. For example, scar tissue on the soft palate may present a continuing irritant to the patient. Moreover, the procedures are not reversible in the event that they induce adverse side effects.

In response to the above problems, medical implants have been developed for treating OSA. For example, the PILLAR™ Palatal Implant System sold by Restore Medical of St. Paul, Minn. is an implantable device that uses several braided PET cylinders that are implanted in the soft palate. The PILLAR device has been associated with a number of adverse side effects, including extrusion, infection, and patient discomfort.

Another implant system sold under the trademark REPOSE™ by InfluENT of Concord, N.H., uses a bone screw that is inserted into the posterior aspect of the mandible at the floor of the mouth. A loop of suture is passed through the base of the tongue and attached to the titanium screw. The REPOSE™ system achieves a suspension or hammock of the base of the tongue, thereby making it less likely that the tongue base will fall back against the pharyngeal wall or soft palate during sleep. Due to the high activity of the tongue during wakefulness, the suture component of this device may cut into the tissue of the tongue (i.e. a "cheese-cutter" effect), causing device failure and requiring subsequent removal. Thus, the duration of beneficial effects afforded by the REPOSE™ implant may only be temporary.

Another implant system for treating OSA, trademark ADVANCE™, is being developed by Aspire Medical, Inc. of Sunnyvale, Calif. The system uses a bone anchor inserted into the mandible and a winged nitinol member implanted in the base of the tongue. Similar to the REPOSE™ system, the ASPIRE™ system may expose the tongue to a "hard stop," i.e., the bone anchor does not move when the tongue moves, which may cause tearing of the tongue tissue (a "cheese-cutter" effect), loosening of the implant, and eventual device failure.

U.S. Pat. No. 7,367,340 assigned to Apneon, Inc. of Cupertino, Calif., discloses an implant that uses magnets for treating OSA. In one embodiment, a first set of magnets are implanted in the back of the tongue and a second set of magnets are implanted in a pharyngeal wall. The respective magnets in the tongue and the pharyngeal wall repel one another for opening the upper airway. Other embodiments involve placing a magnet in the tongue and then coupling this to a magnet placed external to the patient's neck and jaw. The efficacy of such a device is severely compromised by distances between the magnets, even more so in obese patients that may have excess adipose tissue in the inframandibular region.

The prior art tongue suspension systems described above are prone to failure as a result of the "hard-stop" effect that may cause tongue tissue to be incised, excess distances between the respective components, or the potential for components to become misaligned during use. The prior art magnetic implants described above have failed because the magnets are exposed to tissue in a manner that might compress tissue excessively, which may result in tissue damage. Moreover, magnetic implants become ineffective if the magnets migrate or flip. Thus, prior art implants have had limited success and may cause adverse health consequences for patients.

In view of the above results, there remains a need for systems, devices, and methods for safely and effectively treating OSA. There also remains a need for minimally invasive systems, devices, and methods for treating OSA. In addition, there remains a need for systems, devices, and methods for treating OSA that encourage patient compliance, minimize patient discomfort, and achieve long-term, efficacious results.

SUMMARY OF THE INVENTION

In one embodiment, an implant for treating sleep disorders includes a first magnet connectable with bone (e.g. mandible, hyoid, and maxilla) and/or soft tissue (e.g. inframandibular fascia, geniohyoid muscle, genioglossus muscle, and digastrics muscle), and a second magnet connectable with a tongue anchor. In one embodiment, the first magnet is connected with bone or soft tissue and is held at a fixed distance from the bone. If the tongue relaxes toward the pharyngeal wall, the first magnet repels the second magnet for urging the second magnet and the tongue anchor connected therewith toward the bone or soft tissue for opening a patient's upper airway.

The implant desirably includes a support for aligning the first and second magnets relative to one another so that a magnetic pole on the first magnet is in alignment with and opposes a repelling magnetic pole on the second magnet (e.g., south poles of the first and second magnets facing one another). The support element preferably holds the repelling poles of the respective first and second magnets in alignment so that a repelling magnetic force is generated between the opposing first and second magnets. As the first and second magnets approach one another, the repelling magnetic force desirably urges the second magnet away from the first magnet and toward the bone (e.g. mandible). As the second magnet moves toward the bone anchor, the second magnet pulls the tongue anchor toward the bone anchor, which, in turn, resists excessive movement of the tongue towards the pharyngeal wall and allows for a patent airway.

In one embodiment, the support maintains the first magnet at a fixed distance from the bone, aligns a magnetic pole of the first magnet with a repelling magnetic pole of the second magnet, and guides movement of the first and second magnets relative to one another.

In one embodiment, the support includes a tether adapted to hold the first magnet at a fixed distance from the bone. The tether desirably has a first end secured to the mandible via a bone anchor and a second end secured to the first magnet. The first end of the tether may be secured to the bone using a bone anchor such as a bone screw or a bone hook, or any other biocompatible structure used by those skilled in the art for fastening medical devices to bone. Alternatively, the first end of the tether may be secured to the hyoid bone or soft tissue such as muscle in the inframandibular region. In the latter case, the target muscles being the geniohyoid, digastrics, or mylohyoid muscles. When attaching the first end to soft tissue, sutures, clips, glues, or other means known to those skilled in the art of surgery can be used. For example, the first end of the device may have a loop or tag disposed on it to facilitate suturing or clipping into musculature or fascia. Alternatively, the first end may be flared outward to allow for placing it in a tissue plane such as between two muscles. This flared part of the first end may be porous to facilitate tissue ingrowth and securement.

In one embodiment, the support includes an elongated tube having a proximal end, a distal end, and a lumen extending between the proximal and distal ends. The lumen preferably defines an inner diameter of the elongated tube. In this embodiment, the first magnet is preferably disposed within the elongated tube and is adapted to slide along the inner surface of the elongated tube between the proximal and distal ends thereof. The first magnet has an outer diameter that is just slightly less than the inner diameter of the elongated tube. The second magnet is preferably fixed to the elongated tube and has an opening extending therethrough. In one embodiment, the second magnet is fixed to the proximal end of the tube. The tether may pass through the opening in the second magnet for being connected with the first magnet.

Although the present invention is not limited by any particular theory of operation, making the outer diameter of the first magnet just slightly less than the inner diameter of the elongated tube enables the first magnet to move relative to the tube but will prevent the magnetic orientation of the first magnet from flipping. In one embodiment, the first magnet has a length (distance from outer edge of North pole to outer edge of South pole) that is greater than the inner diameter of the tube so that the magnetic orientation of the first magnet cannot flip.

In one embodiment, the tongue anchor is secured to the distal end of the elongated tube, and the tongue anchor and at least a portion of the elongated tube are implanted in the tissue of a tongue. The tongue anchor desirably has a sufficiently large surface area to form a stable connection with the tissue of the tongue so that the tongue anchor and the elongated tube do not move relative to the tongue tissue to cause problems such as the "cheese-cutter" effect described above.

In one embodiment, a shaft has a first end secured to bone and a second end secured to the first magnet so as to hold the first magnet at a fixed distance from the bone. The shaft may be rigid or flexible and is preferably comprised of a non-porous material that excludes tissue ingrowth or attachment. The shaft may be made of any biocompatible material including stainless steel, titanium, tantalum, nitinol, and polymers. In one embodiment, the shaft maintains the first magnet at a consistent, fixed distance from the bone or soft tissue. Alternatively, the first end of the tether may be secured to the hyoid bone or soft tissue such as muscle in the inframandibular region. In the latter case, the target muscles being the geniohyoid, digastrics, or mylohyoid muscles. The second magnet is slideable over the outer surface of the shaft and has an opening adapted to receive the shaft and the second magnet is slideable over an outer surface of the shaft so that the second magnet may move relative to the first magnet, while the first magnet remains at a fixed distance from the bone.

In another embodiment, the tongue anchor is coupled to the second magnet. The tongue anchor may include a bearing surface (area of anchor exposed to the force the tongue may exert as it moves towards the pharyngeal wall) having a sufficiently large surface to stay in place within the tissue of the tongue so as to avoid the "cheese-cutter" effect described above. The tongue anchor may also include at least one thread interconnecting the tongue anchor and the second magnet. Alternatively, two or more threads interconnect the bearing surface of the tongue anchor with the second magnet.

Once implanted, the first and second magnets are oriented relative to one another so as to generate repelling magnetic forces therebetween that operate to resist excessive movement of the tongue towards the posterior pharyngeal wall for maintaining an open passage through the upper airway. During sleep, as the tongue relaxes toward the posterior pharyngeal wall, the tongue anchor initially pulls the second magnet toward the first fixed magnet. As the second magnet approaches the opposing face of the first fixed magnet, a repelling magnetic force is generated between the opposing faces of the magnets. The repelling force gradually increases as the two magnets approach each other. Since the two magnets are tethered to structures on the opposite side of the opposing magnet, the repelling force resists the forces collapsing the airway as the second magnet is pushed away from the first fixed magnet. Because the first magnet is maintained at a fixed distance from a bone, such as the hyoid or mandible, only the second magnet is free to move so that the generated repelling force pushes the second magnet toward the bone. As the second magnet is pushed toward the bone, the second magnet pulls the tongue anchor coupled therewith toward the bone, which, in turn, pulls the tongue away from the posterior pharyngeal wall for opening the upper airway. Alternatively, the first magnet may be anchored to a soft tissue such as any one of the muscles found in the inframandibular region or fascia.

In one embodiment, a magnetic implant for treating sleep apnea includes first and second magnets, a support for holding the first magnet at a fixed distance from a bone (e.g. a mandible), aligning a magnetic pole of the first magnet with a repelling magnetic pole of the second magnet, and guiding movement of the first and second magnets relative to one another. The magnetic implant preferably includes a tongue anchor coupled with the second magnet.

In another embodiment, the support includes a shaft having a first end secured to bone and a second end secured to the first magnet for holding the first magnet at a fixed distance from the bone. The second magnet desirably has an opening adapted to receive the shaft and the second magnet is slideable over an outer surface of the shaft. The tongue anchor is desirably secured to the second magnet. The tongue anchor may include a bearing surface having a sufficiently large surface to avoid migration of the bearing surface and/or the "cheese-cutter" effect described above. The bearing surface is desirably implanted in the tissue of the tongue. The tongue anchor also desirably includes one or more elongated threads or filaments interconnecting the bearing surface and the second magnet.

In yet another embodiment, a magnetic implant for treating sleep apnea includes first and second magnets, a tether extending between the first magnet and the bone for holding the first magnet a fixed distance from the bone, and an elongated tube for aligning a magnetic pole of the first magnet with a repelling magnetic pole of the second magnet and for guiding movement of the first and second magnets relative to one another. The elongated tube is adapted to slide over the first fixed magnet and the second magnet is fixed to the elongated tube for moving with the elongated tube. A tongue anchor is preferably connected to a distal end of the elongated tube.

In still another embodiment, a magnetic implant for treating sleep apnea includes first and second magnets, a shaft having a first end connected with bone and a second end connected with the first magnet for holding the first magnet at a fixed distance from the bone. The implant includes the second magnet having an opening adapted to receive the shaft, whereby the shaft aligns a magnetic pole of the first magnet with a repelling magnetic pole of the second magnet and guides movement of the first and second magnets relative to one another. The implant also includes a tongue anchor coupled with the second magnet. The tongue anchor may include a bearing surface with at least one thread interconnecting the bearing surface and the second magnet. In one embodiment, the second magnet is adapted to slide over an outer surface of the elongated shaft.

As noted herein, the tongue anchor preferably has a sufficiently sized surface area to prevent migration of the tongue anchor or tearing of the tongue tissue after implantation. In one embodiment, the tongue anchor preferably has a surface area of approximately 0.5-5 cm$^2$. In one embodiment, the tongue anchor may include a mesh or pores or openings for promoting tissue in-growth. In one embodiment, the tongue anchor is implanted within a tongue and healing is allowed to occur before forces are exerted upon the tongue anchor. For example, in one embodiment, one or more of the magnets may be deactivated during healing of the tongue anchor. In one embodiment, one or more of the magnets are not coupled with the implant until after healing of the tongue anchor.

In one embodiment, an implant for treating sleep disorders includes a first anchor, a first magnet coupled to the first anchor, a tongue anchor, a second magnet coupled to the tongue anchor, and a support for aligning the first and second magnets so that a repelling force is generated between the magnets for urging the second magnet away from the first magnet. The repelling force may urge the second magnet toward the first anchor. The first anchor may be connected with bone or soft tissue. In one embodiment, the support preferably aligns a magnetic pole of the first magnet with a repelling magnetic pole of the second magnet, and guides movement of the first and second magnets relative to one another. In one embodiment, the support maintains the first magnet at a fixed distance from the first anchor.

In one embodiment, an implant for treating sleep disorders includes first and second magnets, a support for holding the first magnet at a fixed distance from a first anchor, aligning a magnetic pole of the first magnet with a repelling magnetic pole of the second magnet and guiding movement of the first and second magnets relative to one another, and a tongue anchor coupled with the second magnet. The support may include an elongated tube having a proximal end, a distal end, and an inner surface extending between the proximal and distal ends, the inner surface defining an inner diameter of the elongated tube, and the first magnet being disposed within the elongated tube and being adapted to slide over the inner surface of the elongated tube between the proximal and distal ends thereof. In one embodiment, the support includes a shaft having a first end secured to the first anchor and a second end secured to the first magnet for holding the first magnet at the fixed distance from the first anchor. The second magnet has an opening adapted to receive the shaft and the second magnet is slideable over an outer surface of the shaft. The tongue anchor is secured to the second magnet. The tongue anchor may include a bearing surface and at least one thread interconnecting the bearing surface and the second magnet.

In one embodiment, an implant for treating sleep disorders includes first and second magnets, and a support for holding the first magnet at a fixed location relative to an anchor point. The support is preferably adapted for aligning a magnetic pole of the first magnet with a repelling magnetic pole of the second magnet and for guiding movement of the first and second magnets relative to one another. The implant desirably includes a tongue anchor coupled with the support and the second magnet.

In one embodiment, the support includes at least one guide rail extending between the first and second magnets for guiding sliding movement of the magnets relative to one another. The support may include at least one tether connected with the first magnet for holding the first magnet at a fixed distance from bone or soft tissue. In one embodiment, the support includes a pair of tethers that extend laterally from the first magnet for holding the first magnet in a fixed location.

In one embodiment, the implant may include a flexible diaphragm surrounding the first and second magnets. The flexible diaphragm preferably prevents tissue ingrowth around the first and second magnets.

These and other preferred embodiments of the present invention will be described in more detail below.

BRIEF DESCRIPTION OF THE DRAWING

FIGS. 9A and 9B show an implant for treating obstructive sleep apnea, in accordance with one embodiment of the present invention.

DETAILED DESCRIPTION

Figure 1:
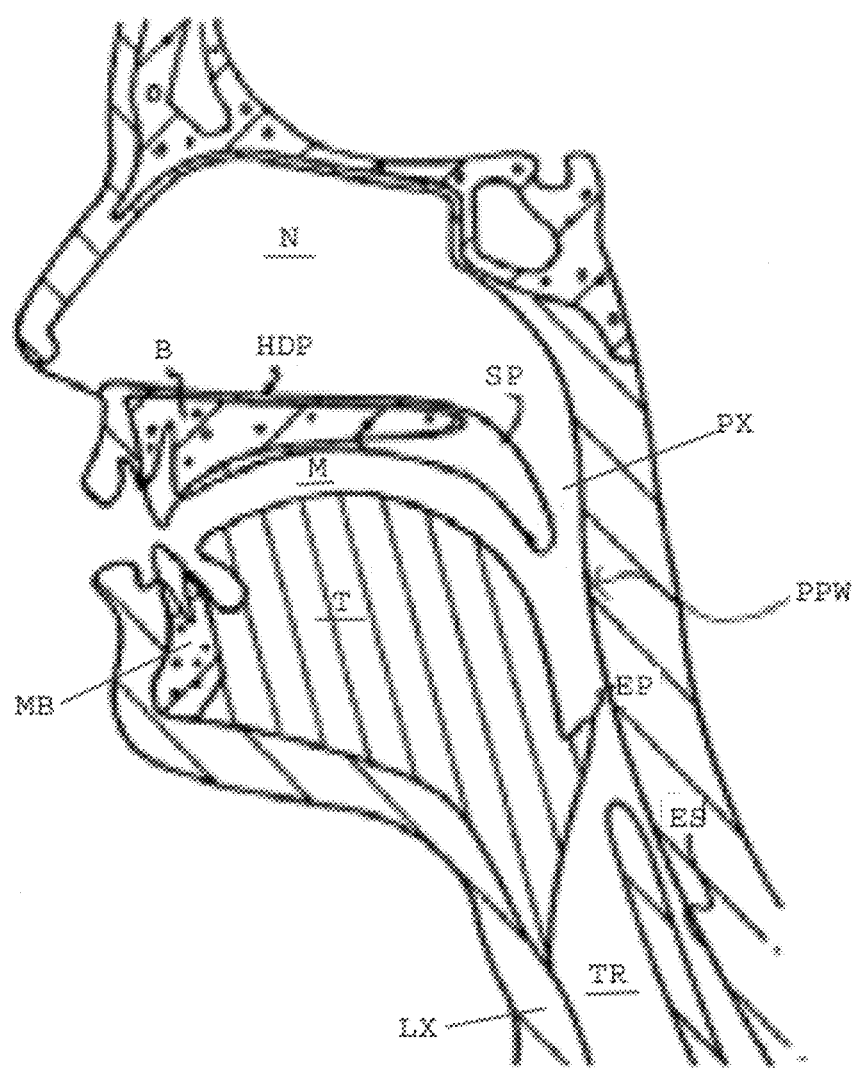
FIG. 1 shows a cross-sectional view of a human head including a nasal cavity and a pharynx.

FIG. 1 shows a cross-section of a human head with anatomical structures including the nasal cavity N, the hard palate HDP including bone B, the soft palate SP, the mouth M, the tongue T, the trachea TR, the epiglottis EP, the esophagus ES, the posterior pharyngeal wall PPW, and the larynx LX. The human head also includes the mandible MB or lower jaw. As used herein, the term mandible is used to cover the bone of the lower jaw, the soft tissue surrounding the lower jaw, and the teeth projecting from the lower jaw.

Figure 2:
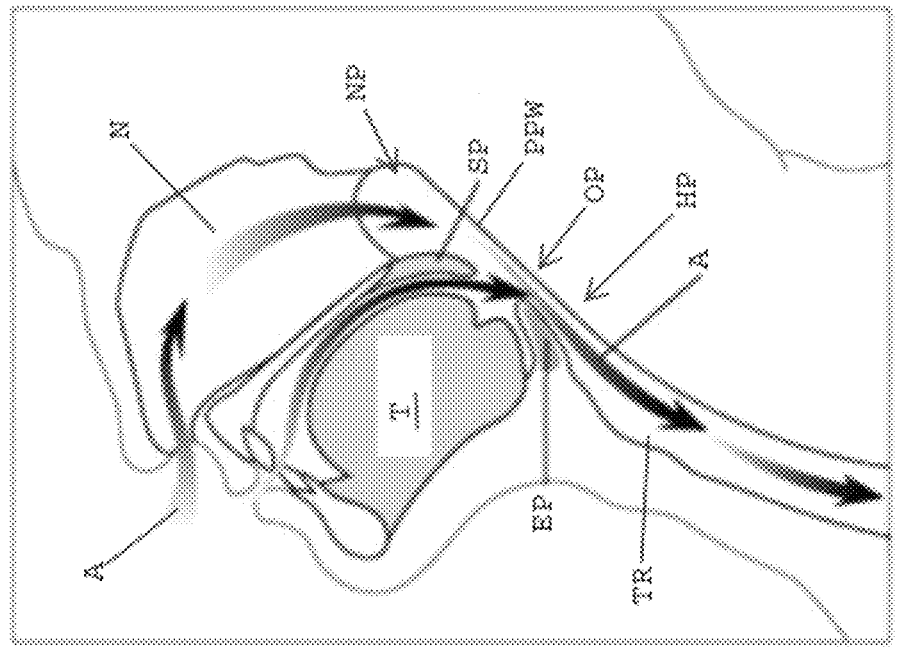
FIG. 2 shows a cross-sectional view of the nasal cavity and the pharynx of a human during normal breathing.

In a human body, the space between the nasal cavity N and the larynx LX is referred to as the upper airway. The most critical part of the upper airway associated with sleep disorders is an air cavity referred to as the pharynx PX. Referring to FIG. 2, the pharynx has three different levels. The nasopharynx NP is the upper portion of the pharynx located in the back of the nasal cavity N. The oropharynx OP is the intermediate portion of the pharynx containing the soft palate SP, the epiglottis EP, and the curve at the back of the tongue T. The oropharynx OP is the section of the pharynx that is most likely to collapse due to the high prevalence soft tissue structure. The hypopharynx HP is the lower portion of the pharynx located below the soft tissue of the oropharynx OP. The hypopharynx HP is in communication with the trachea TR.

As is well known to those skilled in the art, the soft palate and the tongue are both very flexible structures. The soft palate SP provides a barrier between the nasal cavity N and the mouth M. In many instances, the soft palate SP is longer than necessary so that it extends a significant distance between the back of the tongue T and the posterior pharyngeal wall PPW.

Although the muscles of the body relax during sleep, most of the muscles of the respiratory system remain active. During inhalation, the chest wall expands and causes negative pressure to draw air A into the nasal cavity N and the mouth M. The air then flows past the pharynx PX, through the trachea TR and into the lungs. The negative pressure causes the tissue of the upper airway to deform slightly, narrowing the airway passage. In apneic patients, any or all of the muscles that comprise the tongue or soft palate SP may relax excessively, causing them to collapse against the posterior pharyngeal wall PPW to block airflow into the trachea.

Figure 3:
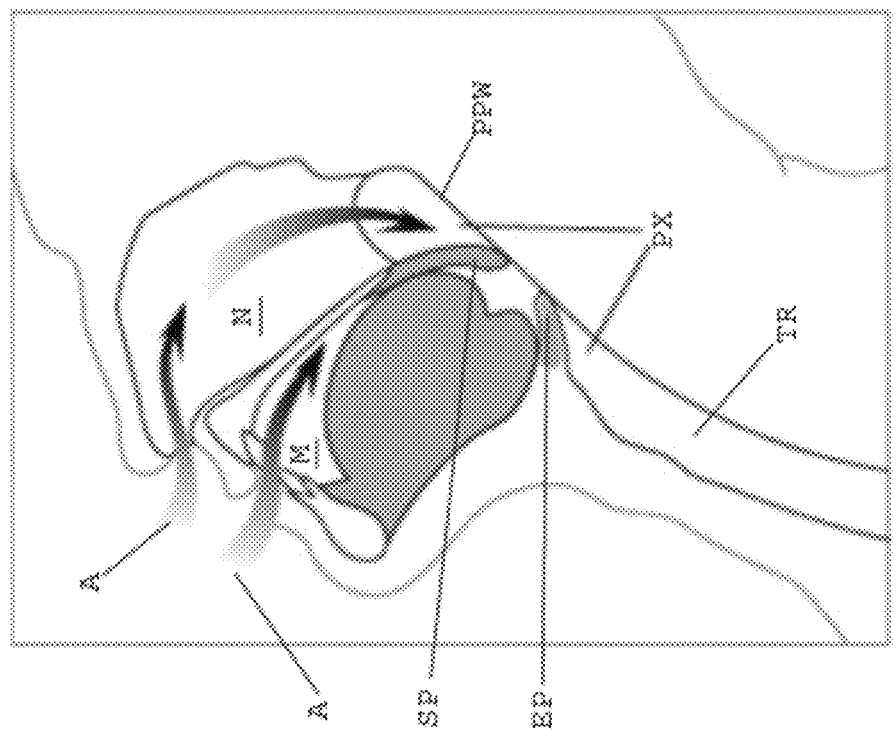
FIG. 3 shows a cross-sectional view of the nasal cavity and the pharynx of a human during an episode of obstructive sleep apnea.

Referring to FIG. 2, when an individual is awake, the back of the tongue T and the soft palate SP maintain their shape and tone due to their respective internal muscles. As a result, the airway, comprised of the nasopharynx NP, the oropharynx OP and the hypopharynx HP, remains open and unobstructed. During sleep, however, the muscle tone decreases so that the back of the tongue and the soft palate become more flexible and distensible. Referring to FIG. 3, without normal muscle tone to keep their shape, the back of the tongue T, the epiglottis EP, and the soft palate SP tend to collapse to block the airway. This condition is commonly referred to as obstructive sleep apnea (OSA).

Figure 4A:
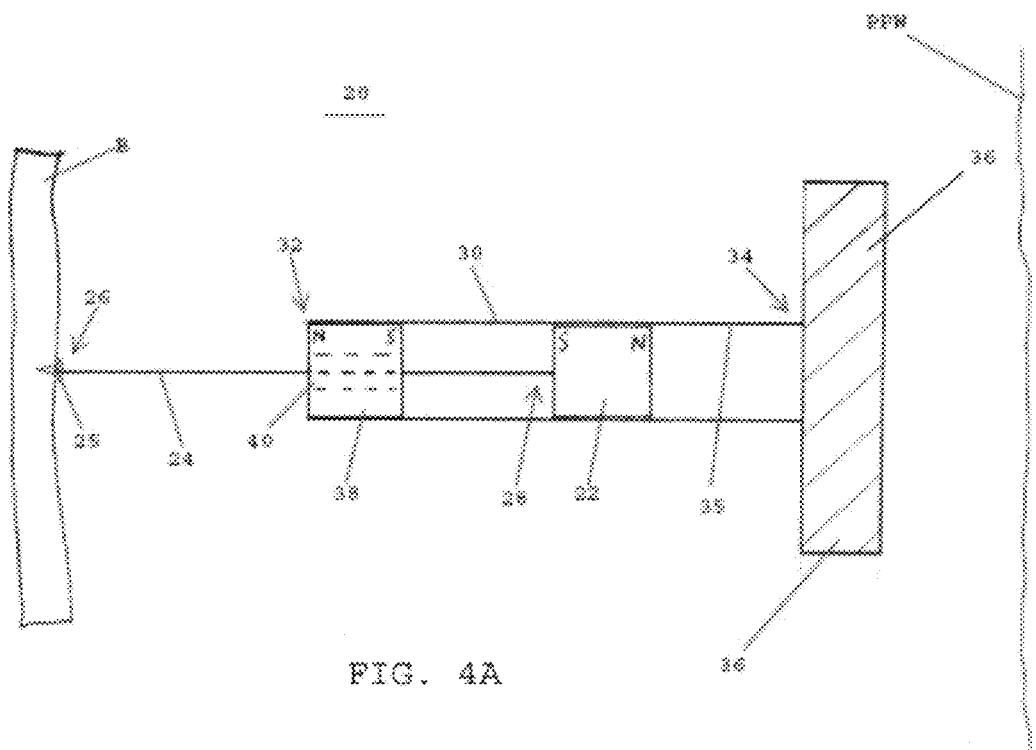
FIG. 4A shows a cross-sectional view of an implant for treating obstructive sleep apnea, in accordance with one embodiment of the present invention.
Figure 4B:
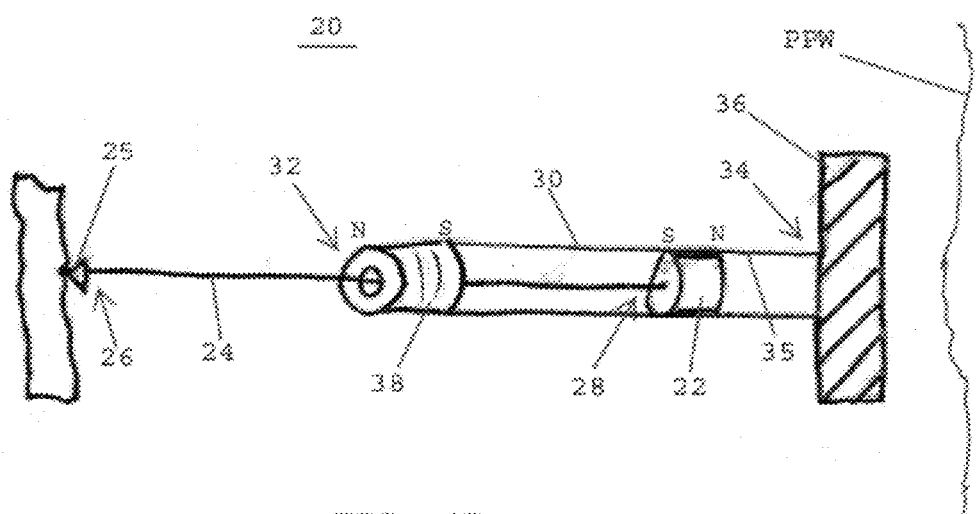
FIG. 4B shows a perspective view of the implant shown in FIG. 4A.

Referring to FIGS. 4A and 4B, in one embodiment, a magnetic implant 20 for treating sleep disorders such as OSA includes a first magnet 22 having a north pole N and a south pole S. The magnetic implant 20 includes a tether 24 having a first end 26 that is secured to bone B (e.g., hyoid bone, maxilla, or mandible) using a bone anchor 25, and a second end 28 that is secured to the first magnet 22. The tether 24 anchors the first magnet 22 to the bone, and has a fixed length between the first and second ends 26, 28 thereof for maintaining the magnet at a fixed distance relative to the bone B. In one embodiment, the distance of the tether 24 is fixed and is about 0.5-3 inches. Although not illustrated in FIGS. 4A and 4B, the first end may alternatively be secured to soft tissue such as fascia or musculature within the inframandibular region of the patient. Suitable tissue includes the geniohyoid, mylohyoid, digastrics, or genioglossus muscles.

The magnetic implant 20 preferably includes a tube 30 having a proximal end 32 and a distal end 34, and an inner surface 35 that extends between the proximal and distal ends 32, 34. The inner surface 35 defines an inner diameter of the tube 30. A tongue anchor 36, implantable in the tissue of a tongue, is secured to the distal end 34 of the tube 30. The magnetic implant 20 includes a second magnet 38 coupled with the tube 30. In one embodiment, the second magnet 38 is preferably fixed to the proximal end 32 of the tube 30 and does not move relative to the tube. The second magnet 38 has a north pole N and a south pole S, and an opening 40 extending between the north and south poles N, S thereof. The tether 24 passes through the opening 40 of the second magnet 38 for being connected with the first magnet 22.

In one embodiment, the tongue anchor is a nitinol "umbrella" that is designed to fit into the midline of a tongue and offer a sufficiently large surface area (0.5-5 cm$^2$) so as to minimize the "cheese-cutting" effect described herein. The tongue anchor may also be a silicone umbrella, a PET umbrella or any other biocompatible implant having dimensions suitable for placement between the neurovascular bundles within the genioglossus muscle. Other preferred materials include PTFE, e-PTFE, polypropylene, polyurethane, polycarbonate, polyethylene terephthalate, nitinol, stainless steel, titanium, tantalum, gold, Polyvinidylene fluoride and combinations thereof.

Referring to FIGS. 4A and 4B, the bone anchor 25 may be a self-tapping bone screw adapted to be imbedded in the mandible. In one embodiment, the bone anchor 25 may be any biocompatible structure commonly used for fastening to bone or soft tissue. In one embodiment, the bone screw has flared nitinol arms, such as a screw sold under the trademark MITEK GN2 device by DePuy Mitek, Inc. Any of the bone or suture anchors known to those skilled in the art of tissue repair can be used. The screw preferably has structure for enabling the length of the screw to be adjusted. In one embodiment, expandable, toggled, or barbed bone anchors may be utilized within the mandible, hyoid, or maxilla to prevent reversal of the bone anchor. In one embodiment, the bone anchor includes one or more adjustable tethers to enable long-term adjustability of the implant.

Referring to FIGS. 4A and 4B, the tube 30, the second magnet 38 secured to the tube 30, and the tongue anchor 36 are adapted to move together as the tongue moves toward and away from the posterior pharyngeal wall PPW. The tube 30, the second magnet 38, and the tongue anchor 36 are also adapted to move relative to the first magnet 22 secured to the tether 24. The first magnet 22 is adapted to slide freely over the inner surface 35 of the tube 30. The first magnet 22 preferably has an outer surface defining an outer diameter that closely matches the inner diameter defined by the inner surface 35 of the tube 30. As a result, the outer surface of the first magnet 22 closely engages the inner surface 35 of the tube 30 so that the orientation of the magnetic poles of the first magnet 22 may not flip. Thus, the close sliding engagement of the outer surface of the first magnet 22 with the inner surface 35 of the tube 30 maintains the magnetic orientation of the poles of the first and second magnets whereby the south pole S of the first magnet and the south pole S of the second magnet remain opposed to one another.

When the magnetic implant 20 is implanted in the tissue of a tongue, the tongue anchor 36 preferably provides a sufficient surface area to form a reliable anchor with the tongue without damaging the tissue of the tongue or causing the cheese-cutter effect. When the tongue moves too far back toward the soft palate or posterior pharyngeal wall PPW, the south pole S of the second magnet 38 initially moves toward the south pole S of the first magnet 22. As the south poles S of the respective magnets move toward one another, the poles repel one another, which forces the second magnet 38 away from the first magnet and toward the bone B, which prevents excessive relaxation of the tongue. The repelling force exerted by the magnets increases according to an inverse of the square of the distance between the magnets 22, 38. As a result, the magnetic implant 20 does not have a "hard stop", and the likelihood of a "cheese-cutting" effect into the tongue musculature is reduced. In addition, the presence of the tube 30 prevents the magnets from flipping.

Figure 5A:
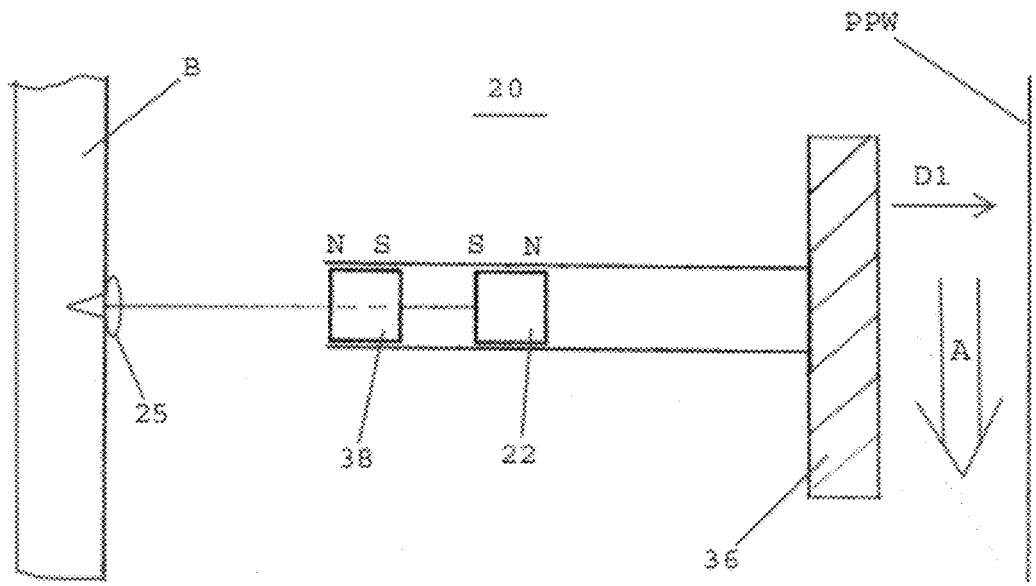
FIG. 5A shows the implant of FIGS. 4A and 4B when a tongue has moved toward a posterior pharyngeal wall in a human, in accordance with one embodiment of the present invention.
Figure 5B:
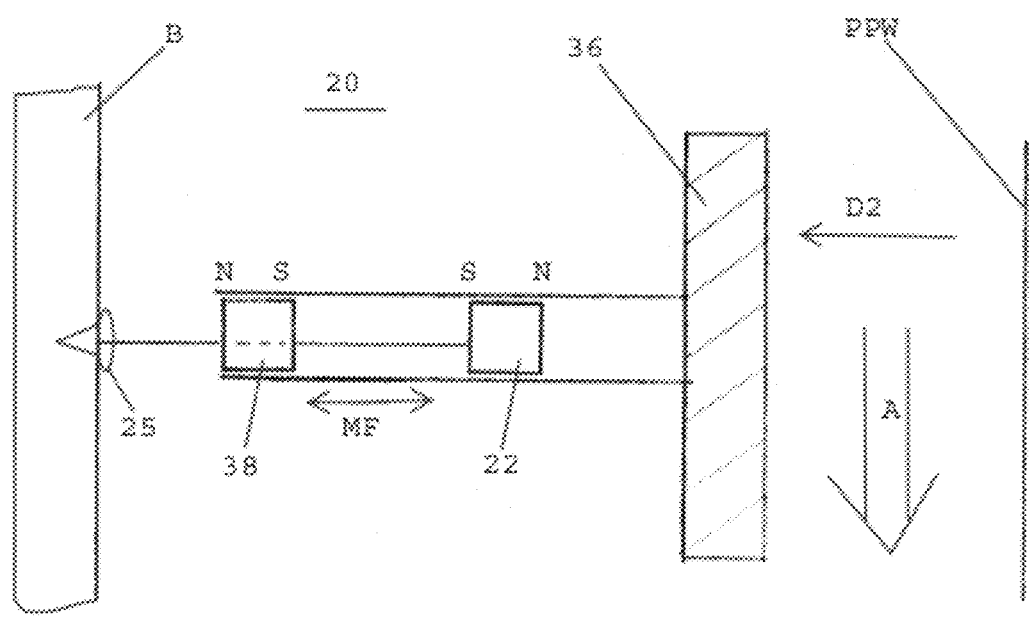
FIG. 5B shows a cross-sectional view of the implant of FIG. 4 as the first and second magnets repel one another for moving the tongue away from the posterior pharyngeal wall.

FIG. 5A shows a cross-sectional view of the magnetic implant 20 of FIGS. 4A and 4B as the tongue relaxes and moves toward the posterior pharyngeal wall PPW for closing an airway. As the tongue relaxes, the south pole S of the second magnet 38 initially approaches the south pole S of the first magnet 22. As noted above, the south poles of the respective first and second magnets 22, 38 repel one another by a repelling force that increases according to an inverse of the square of the distance between the first and second magnets 22, 38. Referring to FIG. 5B, in response to the magnetic forces, the first and second magnets 22, 38 repel one another by a magnetic force designated $M_F$ to pull the tongue anchor 36 in the direction $D_2$, which, in turn, resists excessive movement of the tongue towards the posterior pharyngeal wall PPW. As a result, this allows for opening the airway A between the back of the tongue and the posterior pharyngeal wall PPW.

Figure 6:
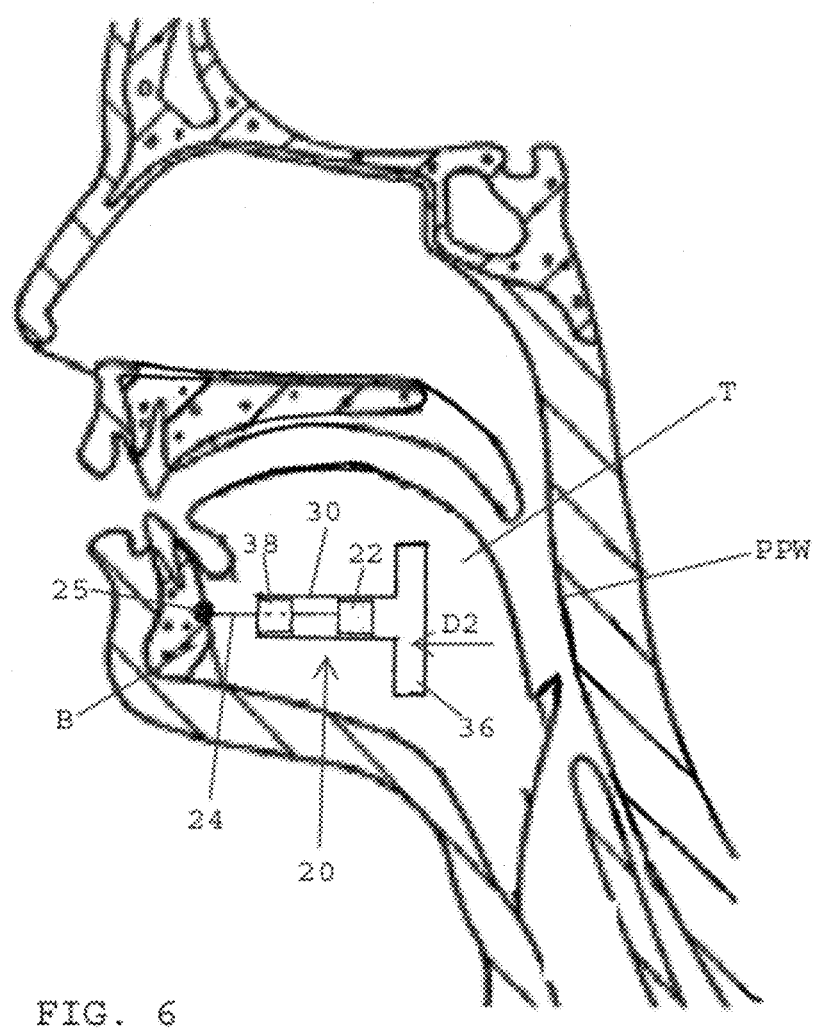
FIG. 6 shows a cross-sectional view of a human head with the implant of FIGS. 4A and 4B implanted in the tongue.

Referring to FIG. 6, in one embodiment, the magnetic implant 20 is implanted within the tissue of a tongue T. The magnetic implant 20 includes the first magnet 22 secured to the mandible or soft tissue via the tether line 24. In one embodiment, the length of the tether 24 is fixed, and is more preferably about 1-3 inches. The first magnet 22 is disposed within the tube 30. The outer surface of the first magnet 22 is preferably in sliding contact with the inner surface of the tube 30 so that the first magnet 22 is able to slide freely over the inner surface of the tube 30. The outer diameter of the first magnet 22 is preferably in close siding engagement with the inner surface of the tube 30 so that the magnetic orientation of the first magnet 22 cannot flip (e.g. whereby the north pole N of the first magnet 22 opposes the south pole S of the second magnet 38). The magnetic implant 20 includes the tongue anchor 36 that implanted within the tissue of the tongue T. The tongue anchor 36 preferably has a sufficient area so that it forms a stable connection relative to the tissue of the tongue T. The magnetic implant 20 includes the second magnet 38 secured to the proximal end 32 of the tube 30. The second magnet 38 has an opening 40 extending therethrough, and the tether 24 passes through the opening 40. Magnets used in any of the embodiments described herein are preferably comprised of rare earth magnets. In addition, these magnets are preferably coated with a biocompatible material such as polypropylene, ultra-high molecular weight polypropylene, or fluoropolymer such as PTFE or Teflon.

Referring to FIG. 6, the magnetic implant 20 preferably keeps the tongue from moving too far toward the posterior pharyngeal wall PPW for closing the airway. If the tongue T moves too far back toward the posterior pharyngeal wall PPW, the south poles S of the respective first and second magnets 22, 38 repel one another, which forces the second magnet 38 and the tongue anchor 36 coupled therewith to move in the direction $D_2$. As the tongue anchor 36 moves in the direction $D_2$, the back of the tongue T moves away from the posterior pharyngeal wall PPW to open the airway.

Figure 7:
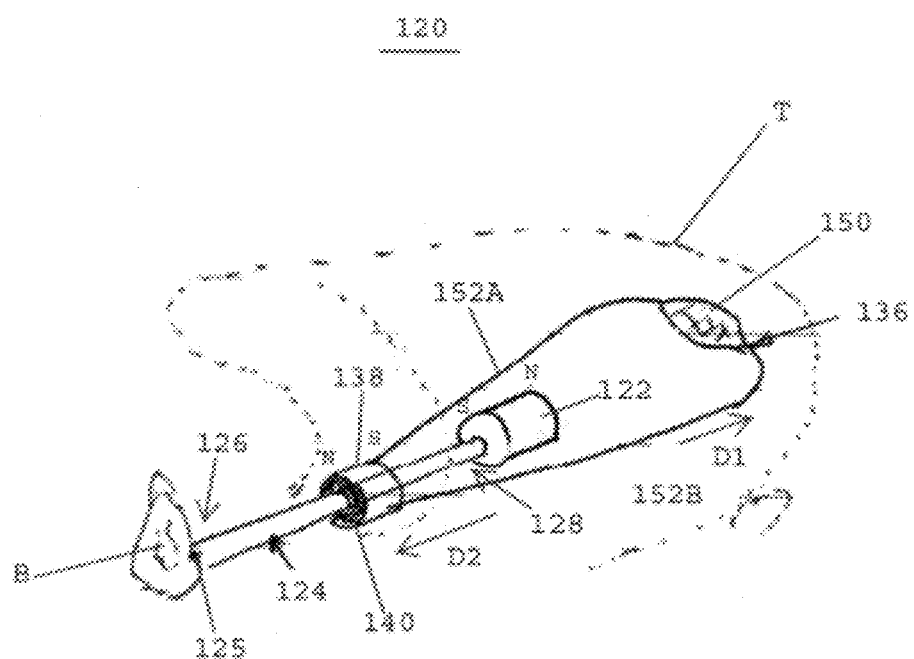
FIG. 7 shows an implant for treating obstructive sleep apnea, in accordance with one embodiment of the present invention.

Referring to FIG. 7, a magnetic implant 120 includes a first magnet 122 having a north pole N and a south pole S. The magnetic implant 120 includes a shaft 124 having a first end 126 anchored to bone B of a patient via a bone anchor 125 and a second end 128 connected to the first magnet 122. The magnetic implant 120 includes a second magnet 138 having a north pole N and a south pole S. The second magnet 138 has an opening 140 passing through a center thereof. The opening 140 preferably extends along an axis that runs between the north and south poles N, S of the second magnet 138.

The shaft 124 is preferably fabricated from a non-resorbable, flexible material such as stainless steel (316L) or nitinol wire, polymer coated stainless steel or nitinol. Other suitable materials include PTFE, PET, polyurethane, or polycarbonate. The shaft 124 holds the first magnet 122 at a fixed distance from the bone B. The shaft 124 preferably engages both the first magnet 122 and the second magnet 138, and maintains the magnetic orientation of the first and second magnets relative to one another. The second magnet is preferably slidably engaged with the shaft 124 and attached to the first magnet. In a highly preferred embodiment, the south poles S of the respective first and second magnets 122, 138 oppose one another.

The magnetic implant 120 includes a tongue anchor 136 used for securing the magnetic implant to the tissue of the tongue. In one embodiment, the tongue anchor 136 has a bearing surface 150 of about 0.5-5 $cm^2$ and is implanted in the tissue of a tongue T. The tongue anchor includes first and second filaments 152A, 152B having proximal ends secured to the second magnet 138 and distal ends secured to the tongue anchor 136. The tongue anchor and the second magnet preferably move together.

After the magnetic implant 120 shown in FIG. 7 is implanted in the tongue, the magnetic implant prevents the tongue from moving too closely to the posterior pharyngeal wall PPW for closing the airway between the tongue and the pharyngeal wall. As the tongue moves in the direction $D_1$, the south poles S of the respective first and second magnets 122, 138 initially move toward one another. In response, the repelling magnetic forces between the first and second magnets force the magnets away from one another so that the second magnet 138 slides along the shaft 124 in the direction $D_2$ toward the bone anchor 125 at the first end 126 of the shaft 124. As the second magnet 138 slides along the shaft 124 in the direction $D_2$, the second magnet 138 pulls the tongue anchor 136 in the direction $D_2$, which, in turn, prevents the tongue from approaching the posterior pharyngeal wall, thus keeping an open airway.

Figure 8:
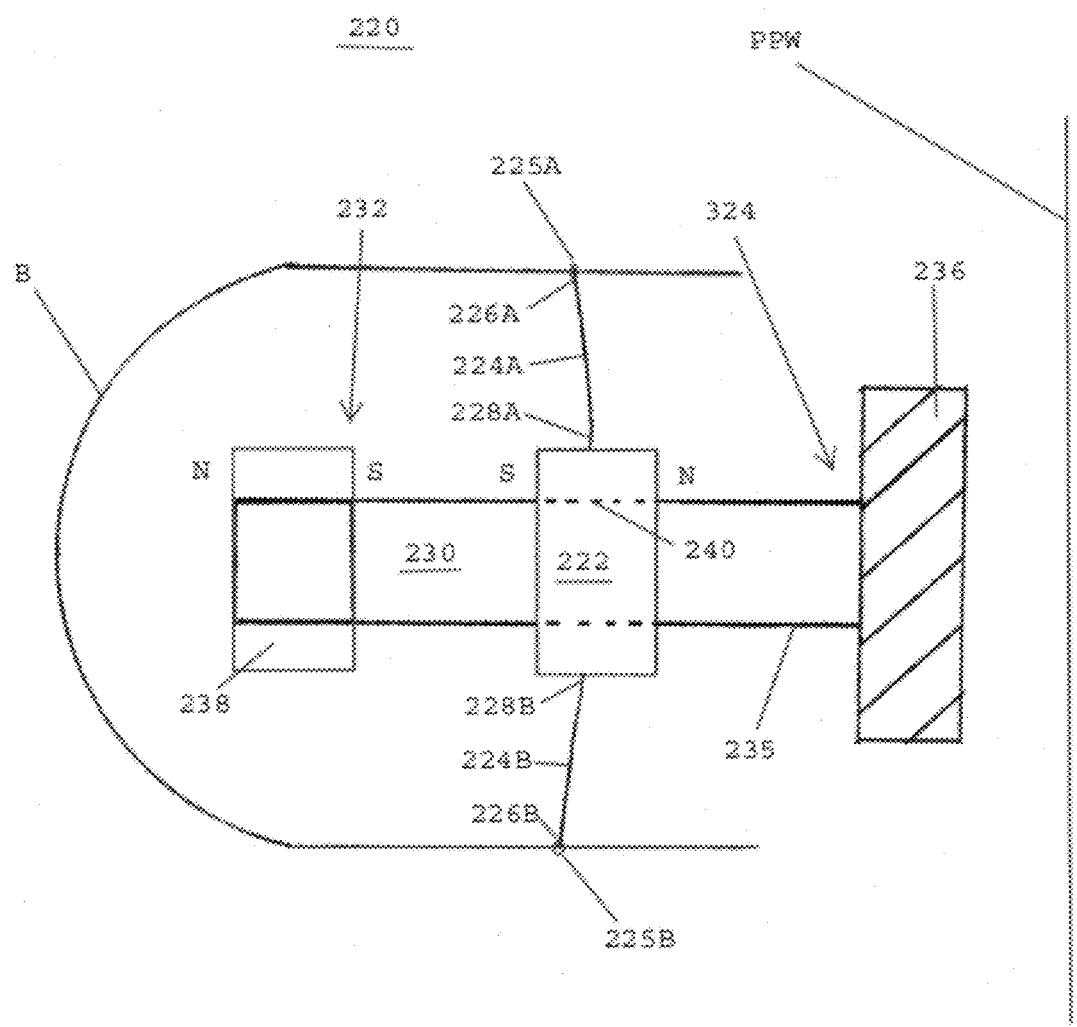
FIG. 8 shows an implant for treating obstructive sleep apnea, in accordance with one embodiment of the present invention.

Referring to FIG. 8, in one embodiment, a magnetic implant 220 for treating sleep disorders such as OSA includes a first magnet 222 having a north pole N and a south pole S. The magnetic implant 220 includes a pair of tethers 224A, 224B having first ends 226A, 226B that are secured to bone B (e.g., hyoid bone, maxilla, or mandible) using bone anchors 225A, 225B, and second ends 228A, 228B that are secured to the first magnet 222. The tethers 224A, 224B anchor the first magnet 222 to the bone, and preferably maintain the first magnet 222 at a fixed distance relative to the bone B. Although not illustrated in FIG. 8, in one embodiment, the first ends 226A, 226B of the tethers 224A, 224B may be secured to soft tissue such as fascia or musculature within the inframandibular region of the patient. Suitable tissue includes the geniohyoid, mylohyoid, digastrics, or genioglossus muscles.

The magnetic implant 220 preferably includes a shaft 230 having a proximal end 232 and a distal end 234, and an outer surface 235 that extends between the proximal and distal ends 232, 234. The outer surface 235 defines an outer diameter of the shaft 230. The first magnet 222 preferably has an opening 240 extending between the north and south poles N, S thereof. The shaft 224 passes through the opening 240 of the first magnet 222 and the first magnet is adapted to slide over the outer surface 235 of the shaft.

A tongue anchor 236, implantable in the tissue of a tongue, is secured to the distal end 234 of the shaft 230. The magnetic implant 220 includes a second magnet 238 coupled with the shaft 230. In one embodiment, the second magnet 238 is preferably fixed to the proximal end 232 of the shaft 230 and does not move relative to the shaft. The second magnet 238 has a north pole N and a south pole S.

The tongue anchor 236, the shaft 230, and the second magnet 238 secured to the shaft 230 are adapted to move together as the tongue moves toward and away from the posterior pharyngeal wall PPW. The tongue anchor 236, the shaft 230, and the second magnet 238 are also adapted to move relative to the first magnet 222 secured to bone B via the pair of tethers 224A, 224B. The first magnet 222 is adapted to slide freely over the outer surface 235 of the shaft 230. In one embodiment, the opening 240 through the first magnet 222 preferably has an inner surface defining an inner diameter that closely matches the outer diameter defined by the outer surface 235 of the shaft 230. As a result, the opening 240 of the first magnet 222 closely engages the outer surface 235 of the shaft 230 so that the orientation of the magnetic poles of the first magnet 222 may not flip. Thus, the close sliding engagement of the opening of the first magnet 222 with the outer surface 235 of the shaft 230 maintains the magnetic orientation of the poles of the first and second magnets whereby the south pole S of the first magnet and the south pole S of the second magnet remain opposed to one another.

After implantation in a tongue, when the tongue moves too far back toward the soft palate or posterior pharyngeal wall PPW, the south pole S of the second magnet 238 initially moves toward the south pole S of the first magnet 222. As the south poles S of the respective magnets move toward one another, the poles repel one another, which forces the second magnet 238 away from the first magnet, which prevents excessive relaxation of the tongue. The repelling force exerted by the magnets increases according to an inverse of the square of the distance between the magnets 222, 238. As a result, the magnetic implant 220 does not have a "hard stop", and the likelihood of a "cheese-cutting" effect into the tongue musculature is reduced. In addition, the presence of the shaft 230 prevents the magnets from flipping.

Referring to FIGS. 9A and 9B, in one embodiment, a magnetic implant 320 for treating sleep disorders such as OSA includes a first magnet 322 having a north pole N and a south pole S, and a second magnet 338 having a north pole N and a south pole S that opposes the south pole of the first magnet. The first and second magnets 322, 338 are disposed within a flexible diaphragm 325 (e.g. a bellow-like structure) that surrounds the magnets for preventing tissue ingrowth. The magnetic implant 320 includes a first shaft 324 having a first end 326 including an anchor 325 that is securable to bone B (e.g., hyoid bone, maxilla, or mandible), and a second end 328 including a pair of first guide rails 329A, 329B that pass through openings 372A, 372B for being secured to the first magnet 322. The first shaft 324 and the first guide rails 329A, 329B anchor the first magnet 322 to bone or soft tissue (not shown). The first shaft 324 preferably has a fixed length between the first and second ends 326, 328 thereof for maintaining the first magnet at a fixed distance relative to the bone or soft tissue. In one embodiment, the length of the first shaft 324 is fixed and is about 0.5-3 inches. As noted above, the first end 326 of the first shaft 324 may be secured to soft tissue such as fascia or musculature within the inframandibular region of the patient. Suitable tissue includes the geniohyoid, mylohyoid, digastrics, or genioglossus muscles.

The magnetic implant 320 preferably includes a second shaft 330 having a proximal end 332 and a distal end 334. The proximal end 332 of the second shaft 330 has a pair of second guide rails 333A, 333B projecting therefrom. The second guide rails 333A, 333B preferably pass through respective openings 374A, 374B in the first magnet 322 and are connected with the second magnet 338. The magnetic implant 320 includes a tongue anchor 336, implantable in the tissue of a tongue that is secured to the distal end 334 of the second shaft 330.

The flexible diaphragm 370 preferably has a first end 380 that is sealed over the first shaft 324 and a second end 382 that is sealed over the second shaft 330. The diaphragm 370 is preferably flexible for enabling the first and second magnets 322, 338 to move relative to one another inside the diaphragm. The sealed ends 380, 382 of the diaphragm 370 prevent tissue ingrowth inside the diaphragm.

Referring to FIG. 9B, the tongue anchor 336, the second shaft 330, and the second magnet 338 are adapted to move together as the tongue moves toward and away from the posterior pharyngeal wall PPW (not shown). The tongue anchor 336, the second shaft 330, and the second magnet 338 are also adapted to move relative to the first magnet 322 secured to the first shaft 324. The second magnet 338 is adapted to slide freely over the first guide rails 329A, 329B projecting from the first shaft 324, and the first magnet 322 is adapted to slide freely over the second guide rails 333A, 333B. In one embodiment, the outer diameters of the first and second guiderails closely match the size of the openings extending through the first and second magnets 322, 338 so that the orientation of the magnetic poles of the magnets relative to one another does not flip. Thus, the close sliding engagement of the first and second magnets with the guide rails maintains the magnetic orientation of the poles of the first and second magnets whereby the south pole S of the first magnet and the south pole S of the second magnet remain opposed to one another.

After implantation in a tongue, when the tongue moves too far back toward the soft palate or posterior pharyngeal wall PPW, the south pole S of the second magnet 338 initially moves toward the south pole S of the first magnet 322. As the south poles S of the respective magnets move toward one another, the poles repel one another, which forces the second magnet 338 away from the first magnet, which in turn moves the back of the tongue away from the pharyngeal wall. The repelling force exerted by the magnets increases according to an inverse of the square of the distance between the magnets 322, 338. As a result, the magnetic implant 320 does not have a "hard stop", and the likelihood of a "cheese-cutting" effect into the tongue musculature is reduced. In addition, the presence of the guide rails 329A, 329B, 333A, 333B prevents the magnets from flipping.

Although various embodiments disclosed herein relate to use in humans, it is contemplated that the present invention may be used in all mammals, and in all animals having air passages. Moreover, the implants disclosed herein may incorporate any materials that are biocompatible, as well as any solutions or components that minimize rejection, enhance tissue in-growth, and improve acceptance of the implants after the implants have been implanted.

The present application discloses particular embodiments of a magnetic implant implantable in a tongue for preventing obstructive sleep apnea. The present invention is not limited by the particular embodiments shown and described herein. It is contemplated that the configuration of the magnets and the supporting elements for the magnets may change and still fall within the scope of the present invention. In its broadest concept, the present invention covers all implants that use the repelling forces between magnets to move the tongue away from the pharyngeal wall or soft palate opening an airway through a direct interaction with structures anterior to the anchor placed within the tongue. The present invention also covers all structures that maintain the repelling faces of magnets in alignment with one another for moving a body part to open an airway.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures.

While the foregoing is directed to embodiments of the present invention, other and further embodiments of the invention may be devised without departing from the basic scope thereof. As such, the scope of the present invention is to be limited only as set forth in the appended claims.

What is claimed is:
1. An implant for treating sleep disorders comprising:
   a first anchor;
   a first magnet coupled to said first anchor;
   a tongue anchor; a second magnet coupled to said tongue anchor;
   and a support for aligning said first and second magnets so that a repelling force is generated between said magnets for urging said second magnet away from said first magnet
   wherein said repelling force urges said second magnet toward said first anchor.

2. The implant as claimed in claim 1, wherein said first anchor is adapted to be connected with bone or soft tissue.

3. The implant as claimed in claim 2, wherein said bone is selected from the group consisting of mandible, hyoid, and maxilla, and said soft tissue is selected from the group consisting of the inframandibular fascia, geniohyoid muscle, genioglossus muscle, and digastrics muscle.

4. The implant as claimed in claim 1, wherein said support aligns a magnetic pole of said first magnet with a repelling magnetic pole of said second magnet, and guides movement of said first and second magnets relative to one another.

5. The implant as claimed in claim 4, wherein said support maintains said first magnet at a fixed distance from said first anchor.

6. The implant as claimed in claim 5, wherein said support comprises an elongated tube having a proximal end, a distal end, and an inner surface defining an inner diameter extending between the proximal and distal ends.

7. The implant as claimed in claim 6, wherein said first magnet has an outer diameter that is slightly smaller than the inner diameter of said elongated tube.

8. The implant as claimed in claim 7, further comprising a tether for coupling said first magnet with said first anchor, said tether having a first end connected with said first anchor and a second end connected with said first magnet.

9. The implant as claimed in claim 8, wherein said tongue anchor is secured to the distal end of said elongated tube, said second magnet is fixed to said elongated tube and has an opening extending therethrough, and said tether passes through the opening in said second magnet.

10. The implant as claimed in claim 5, wherein said support comprises a shaft having a first end secured to said first anchor and a second end secured to said first magnet for holding said first magnet at the fixed distance from said first anchor.

11. The implant as claimed in claim 10, wherein said shaft is flexible and comprises biocompatible materials selected from the group consisting of stainless steel, titanium, tantalum, nitinol, and polymers.

12. The implant as claimed in claim 10, wherein said second magnet has an opening adapted to receive said shaft and said second magnet is slideable over an outer surface of said shaft, and wherein said tongue anchor is secured to said second magnet, said tongue anchor comprising a bearing surface and at least one thread interconnecting said tongue anchor and said second magnet.

13. An implant for treating sleep disorders comprising:
   first and second magnets;
   a support for holding said first magnet at a fixed distance from a first anchor, aligning a magnetic pole of said first magnet with a repelling magnetic pole of said second magnet and guiding movement of said first and second magnets relative to one another;
   and a tongue anchor coupled with said second magnet wherein the repelling magnetic pole of said second magnet urges said second magnet toward the first anchor.

14. The implant as claimed in claim 13, wherein said support comprises an elongated tube having a proximal end, a distal end, and an inner surface extending between the proximal and distal ends, the inner surface defining an inner diameter of said elongated tube, and wherein said first magnet is disposed within said elongated tube and is adapted to slide over the inner surface of said elongated tube between the proximal and distal ends thereof.

15. The implant as claimed in claim 14, wherein said tongue anchor is secured to the distal end of said elongated tube, and wherein said tongue anchor and said elongated tube are implantable in a tongue.

16. The implant as claimed in claim 14, wherein said support further comprises a tether adapted to hold said first magnet at the fixed distance from said first anchor, said tether having a first end secured to said first anchor and a second end secured to said first magnet, and wherein said second magnet is fixed to said elongated tube and has an opening extending therethrough and said tether passes through the opening in said second magnet.

17. The implant as claimed in claim 13, wherein said support comprises a shaft having a first end secured to said first anchor and a second end secured to said first magnet for holding said first magnet at the fixed distance from said first anchor, and wherein said second magnet has an opening adapted to receive said shaft and said second magnet is slideable over an outer surface of said shaft.

18. The implant as claimed in claim 17, wherein said tongue anchor is secured to said second magnet, and wherein said tongue anchor comprises a bearing surface and at least one thread interconnecting said bearing surface and said second magnet.

19. An implant for treating sleep disorders comprising:
first and second magnets;
a support for holding said first magnet at a fixed location relative to a first anchor point; said support being adapted for aligning a magnetic pole of said first magnet with a repelling magnetic pole of said second magnet and for guiding movement of said first and second magnets relative to one another; and a tongue anchor coupled with said support and said second magnet;
wherein the repelling magnetic pole of said second magnet urges said second magnet toward the first anchor point.

20. The implant as claimed in claim 19, wherein said support comprises at least one guide rail extending between said first and second magnets for guiding sliding movement of said magnets relative to one another.

21. The implant as claimed in claim 19, wherein said support comprises at least one tether connected with said first magnet for holding said first magnet at a fixed distance from bone or soft tissue.

22. The implant as claimed in claim 19, further comprising a flexible diaphragm surrounding said first and second magnets.

23. The implant as claimed in claim 19, wherein said support comprises:
an elongated tube having a proximal end, a distal end, and an inner surface extending between the proximal and distal ends, the inner surface defining an inner diameter of said elongated tube;
and said first magnet being disposed within said elongated tube and being adapted to slide along the inner surface of said elongated tube between the proximal and distal ends thereof, and wherein said first magnet has an outer diameter that is slightly smaller than the inner diameter of said elongated tube.

24. The implant as claimed in claim 23, wherein said second magnet is fixed to said elongated tube and has an opening extending therethrough, and wherein a tether connected to said first magnet passes through the opening in said second magnet.

25. An implant for treating sleep disorders comprising:
a first anchor;
a tether;
a first magnet coupled to said first anchor by said tether;
a tongue anchor;
a second magnet coupled to said tongue anchor;
and a support for aligning said first and second magnets so that a repelling force is generated between said magnets for urging said second magnet away from said first magnet;
wherein said second magnet has an opening extending therethrough, and said tether passes through the opening in said second magnet.

26. An implant for treating sleep disorders comprising:
first and second magnets;
a support for holding said first magnet at a fixed distance from a first anchor, aligning a magnetic pole of said first magnet with a repelling magnetic pole of said second magnet and guiding movement of said first and second magnets relative to one another;
and a tongue anchor coupled with said second magnet;
wherein said support further comprises a tether adapted to hold said first magnet at the fixed distance from said first anchor, said tether having a first end secured to said first anchor and a second end secured to said first magnet, and wherein said second magnet has an opening extending therethrough and said tether passes through the opening in said second magnet.

27. An implant for treating sleep disorders comprising:
first and second magnets;
a support for holding said first magnet at a fixed location relative to an anchor point; said support being adapted for aligning a magnetic pole of said first magnet with a repelling magnetic pole of said second magnet and for guiding movement of said first and second magnets relative to one another; and a tongue anchor coupled with said support and said second magnet;
wherein said second magnet has an opening extending therethrough, and wherein a tether connected to said first magnet passes through the opening in said second magnet.

* * * * *